United States Patent [19]

Augier et al.

[11] Patent Number: 5,736,246

[45] Date of Patent: Apr. 7, 1998

[54] REINFORCING GLASS STRANDS AND COMPOSITES RESISTANT TO CORROSIVE MEDIA

[75] Inventors: Eric Augier, Barberaz; Didier Muller, La Ravoire; Michel Arpin, La Motte Servolex, all of France

[73] Assignee: Vetrotex France, Aubervilliers Cedex, France

[21] Appl. No.: 705,683

[22] Filed: Aug. 29, 1996

[30] Foreign Application Priority Data

Sep. 1, 1995 [FR] France .................................. 95 10316

[51] Int. Cl.$^6$ .................................. B32B 9/00; C08K 9/06
[52] U.S. Cl. .................. 428/392; 428/375; 428/378; 428/392; 428/428; 523/214; 556/419
[58] Field of Search .................................. 428/392, 391, 428/378, 375; 556/419, 413, 423, 424; 523/214, 216, 217

[56] References Cited

U.S. PATENT DOCUMENTS 3,956,353  5/1976  Plueddemann .

*Primary Examiner*—Patrick Ryan
*Assistant Examiner*—J. M. Gray
*Attorney, Agent, or Firm*—Oblon, Spivak, McClelland, Maier & Neustadt, P.C.

[57] ABSTRACT

A sizing composition is provided that includes at least one silane satisfying the following formula:

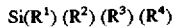

$$Si(R^1)(R^2)(R^3)(R^4)$$

wherein:

$R^1$ and $R^2$ are each, independently, an alkoxy group;

$R^3$ is an alkoxy group or a hydrocarbon radical that optionally contains one or more nitrogens;

$R^4$ is a hydrocarbon radical that optionally contains one or more nitrogens, and includes at least one unsaturated ring substituted with at least one unsaturated chain conjugated with the unsaturated ring, that is useful for coating glass strands for reinforcement of organic or inorganic materials, the glass strands coated with such sizing compositions and the reinforced composite materials prepared therefrom, having improved corrosion resistance, particularly in alkaline media.

21 Claims, No Drawings

REINFORCING GLASS STRANDS AND COMPOSITES RESISTANT TO CORROSIVE MEDIA

BACKGROUND OF THE INVENTION

The present invention relates to a size composition for coating glass strands (or "fibers") intended for reinforcing organic and/or inorganic materials, wherein the coated strands and/or the reinforced materials are capable of being used in corrosive media (humidity, NaCl salty medium, acid medium or alkaline medium), the glass strands thus coated and the reinforced products (or "composites") obtained from the strands.

DISCUSSION OF PRIOR ART

Glass strands have been used to reinforce organic and/or inorganic materials for a long time. The strands most commonly employed are E glass strands having a composition derived from the eutectic composition of the $SiO_2$—$A_2O_3$—$CaO$ system at 1170° C. These strands are usually coated during their manufacture with a sizing composition primarily intended to protect the strands from abrasion and to promote adhesion between the glass and the material which the glass strands are intended to reinforce. This good adhesion particularly contributes to obtaining composites that have good mechanical properties. The E glass strands thus sized are particularly suitable to be combined with thermoplastic or thermosetting organic materials for producing composites having good mechanical properties. However, in certain corrosive media, such as when these strands are combined directly (i.e. without being protected by an organic material) with a alkaline material such as cement or when the composites produced from these strands are subjected to high mechanical stresses in certain corrosive media, especially in cement or in installations in permanent contact with water, salt or acid, these strands are degraded and their mechanical properties deteriorate, leading to a decrease in their reinforcing effect over time.

Various attempts have been made to solve this problem. One attempt was to modify the composition of the glass of which the strands are composed to try to improve the chemical resistance of the strands with respect to a highly alkaline medium. The composition of these glasses, called alkali-resistant glasses, generally contains a high proportion of zirconium oxide and is, for example, of the $Na_2O$—$ZrO_2$—$SiO_2$ type. A conventional composition of these glasses is described in GB 1,290,528.

However, although these glasses are attacked less in a alkaline medium than E glass, their degradation is only slowed down and the decrease in their mechanical properties can be significant under certain conditions. Additionally, the use of such strands is currently limited to the direct reinforcement of cement. These strands, even coated with common sizes, such as those used to improve the adhesion of E glass strands to organic materials, adhere less strongly to organic materials than E glass strands and consequently are of more limited benefit in reinforcing the latter materials. Even when these strands are coated with conventional sizes, such as those used to coat E glass strands to render them suitable for weaving, they can only be woven with considerable difficulty.

It is also known to coat glass strands intended for reinforcing cement with a primer. The aim of the primer composition is to protect the surface of the strands from attack by the cement. Here too, many formulations have been proposed, such as coating the strands with a furan resin. However, most of these formulations merely provide very temporary protection.

Other solutions, such as the addition of agents that reduce the basicity of the media in which the strands are found, relate only to specific applications and are therefore of very limited scope. It is also known to use other reinforcement materials (carbon strands, etc.) to produce composites that are resistant to corrosive media. However, the cost of such reinforcement materials remains high compared to glass strands and their application remains limited.

SUMMARY OF THE PRESENT INVENTION

Accordingly, one object of the present invention is to provide glass strands whose reinforcement effect is greater and/or better maintained over time in at least one of the following corrosive media: wet medium, NaCl salty medium, acid medium, alkaline medium.

A further object of the present invention is to provide glass strands which may advantageously be combined with organic and/or inorganic materials to obtain composites having one or more improved mechanical properties before and after ageing, for at least a certain period of time, in at least one of the following corrosive media: wet medium, NaCl salty medium, acid medium, alkaline medium.

Another object of the present invention is to provide glass strands whose degradation in at least one of the above corrosive media is more greatly slowed down (i.e. has a less rapid fall in the mechanical properties of the composites obtained from the strands) compared to conventional glass strands.

Another object of the present invention is to provide reinforced products or composites having improved mechanical properties, that contain the present glass strands.

Another object of the present invention is to provide a size composition useful for protecting glass strands from the degrading effects of corrosive media.

These and other objects of the present invention have been satisfied by the discovery of a sizing composition comprising a silane satisfying the following formula:

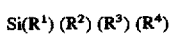
$Si(R^1) (R^2) (R^3) (R^4)$ wherein:
$R^1$ and $R^2$ are each, independently, an alkoxy group;
$R^3$ is an alkoxy group or a hydrocarbon radical that optionally contains one or more nitrogens;
$R^4$ is a hydrocarbon radical that optionally contains one or more nitrogens, and includes at least one unsaturated ring substituted with at least one unsaturated chain conjugated with the unsaturated ring;

and its use in coating glass strands for reinforcement of organic and/or inorganic materials and providing corrosion resistance thereto.

DETAILED DESCRIPTION OF THE PREFERRED EMBODIMENTS

The glass strands according to the present invention are coated with a sizing composition comprising at least one silane satisfying the following formula:

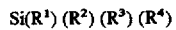
$Si(R^1) (R^2) (R^3) (R^4)$ in which:
$R^1$ and $R^2$, independently, are alkoxy groups
$R^3$ is an alkoxy group or a hydrocarbon radical that optionally contains nitrogen;

$R^4$ is a hydrocarbon radical that optionally contains nitrogen, and includes at least one unsaturated ring substituted with at least one unsaturated chain conjugated with the ring.

The present invention also relates to the sizing composition used to coat the strands, this composition comprising at least one silane satisfying the above-defined formula.

Within the context of the present invention, the phrase "Composition which includes . . . " is understood to mean a "composition in which one of the initial constituents is . . . ", independently of the change in this constituent within the composition. Likewise, the phrase "glass strands coated with" is understood to mean "glass strands which have been coated with . . . ", independently of the future of the coating after the usual treatments undergone by the glass strands, especially after the drying and/or polymerization operations. Further, the phrase "hydrocarbon radical that optionally contains one or more nitrogens" is understood to mean a radical based only on carbon, hydrogen and possibly nitrogen.

The glass strands according to the invention can be prepared according to conventional processes. In general, the manufacture of glass strands according to the present invention can be performed in the following manner: streams of molten glass are mechanically drawn into the form of one or more fans of continuous filaments from the nozzles of one or more bushings, and then the filaments are coated with the sizing composition according to the present invention before being assembled into one or more strands. Next, these strands can be wound onto rotating supports before being subjected to other operations (extraction with a view to indirect chopping, weaving, etc.) or be distributed on moving conveyors or be chopped after formation by the device used to draw them (direct chopping under the bushing). The presentation of the strands thus varies depending on the intended end use.

The glass strands according to the present invention are preferably presented in the form of wound packages of continuous strands (rovings, cakes, cops, etc.), in the form of chopped strands, mats (sheets of intertwined continuous strands), braids, tapes or nets, with the various strands being preferably composed of filaments having a diameter of between 5 and 24 μm.

The glass strands according to the present invention can be obtained from any type of glass normally used to manufacture reinforcing glass strands. The present strands are preferably strands of E glass, strands of glass of the type called "R glass" (mechanically strong) or "S glass" based on silica, alumina, magnesia and possibly lime or strands of alkali-resistant glass. When the present glass strands are E glass strands, they are preferably obtained from a glass which comprises mainly the following components, in proportions expressed in percentages by weight: 52–58% $SiO_2$; 12–16% $Al_2O_3$; 16–25% CaO; 4–13% $B_2O_3$; 0–6% MgO; 0–2% of alkali-metal oxides (essentially $Na_2O$ and/or $K_2O$). This glass may also include other components, such as fluorine, $TiO_2$, CuO, BaO, ZnO, $ZrO_2$, $LiO_2$, $SO_3$, etc. in proportions not exceeding 1% for each of the components. Other glasses also capable of being used to produce reinforcing strands, but less frequently used in this application, can also be mentioned, especially chemically resistant glasses having the following main composition, in percentages by weight: 57–59% $SiO_2$; 11–13% $Al_2O_3$; 20–22% CaO; 2–5% MgO; 0–0.5% $B_2O_3$; 2–3% $TiO_2$; 0–3% ZnO; 0-9-1% $Na_2O$ and/or $K_2O$; or glasses resistant to acid medium having the following main composition in percentage by weight: 60–66% $SiO_2$; 2–6% $Al_2O_3$; 14–15% CaO; 1–3% MgO; 2–7% $B_2O_3$; 7–10% $Na_2O$ and/or $K_2O$; 0–0.4% $Fe_2O_3$.

Preferably, the glass strands according to the invention are strands of glass called "alkali-resistant" glass. Alkali-resistant glass generally contains zirconium oxide $ZrO_2$. These strands can be chosen from any conventional "alkali-resistant" glass strands (such as those described in GB 1,290,528, U.S. Pat. No. 4,345,037, U.S. Pat. No. 4,036,654, U.S. Pat. No. 4,014,705, and U.S. Pat. No. 3,859,106) and preferably include at least 5 mol % of $ZrO_2$. According to one embodiment of the present invention, the constituent glass of which the strands are composed includes $SiO_2$, $ZrO_2$ and at least one alkali-metal oxide, preferably $Na_2O$, as the main constituents.

An alkali-resistant glass composition preferably used to produce the glass strands according to the present invention is the composition described in GB 1,290,528, composed mainly of the following components in proportions expressed in molar percentages: 62–75% $SiO_2$; 7–11% $ZrO_2$; 13–21% $R_2O$; 1–10% R'O; 0–4% $Al_2O_3$; 0–6% $B_2O_3$; 0–5% $Fe_2O_3$; 0–2% $CaF_2$; 0–4% $TiO_2$; where $R_2O$ represents one or more alkali-metal oxides, preferably $Na_2O$, and, optionally, up to 2% $Li_2O$; and R'O is one or more components chosen from the alkaline-earth metal oxides, ZnO and MnO. The alkali-resistant glass strands according to the present invention particularly meet the objectives of the invention, as explained later.

The sizing composition coating the strands of the present invention can be an aqueous or anhydrous composition or it may comprise, for example, less than 5% by weight of compounds acting solely as a solvent. In most cases, the present sizing composition is an aqueous composition which includes between 70 and 98% by weight of water and is in the form of an aqueous dispersion (emulsion, suspension, mixture of emulsions and/or of suspensions) or of a solution.

The present sizing composition comprises at least one silane satisfying the formula $Si(R^1)(R^2)(R^3)(R^4)$ where $R^1$–$R^4$ are as noted above. Reinforcement of organic and/or inorganic materials, using glass strands coated with a sizing composition which includes one or more of the present silanes, makes it possible to obtain composites having one or more improved mechanical properties before and, for at least a certain time, after ageing, in at least one of the following corrosive media: wet, NaCl salt, acid, and alkaline medium and/or makes it possible to obtain composites whose mechanical properties are better maintained over time (i.e. have a less rapid fall in the mechanical properties), with the observed improvement depending on the type of glass strands coated, on the material reinforced and on the corrosive medium in question.

Within the context of the present invention, "Improved mechanical properties" is understood to mean mechanical properties which are improved compared to those obtained with the same strands that are not coated with the size according to the present invention, especially the same strands coated with a common size which includes, as silane, a silane other than that in accordance with the present invention.

Particular benefit is obtained when the glass strands according to the present invention are alkali-resistant glass strands. In this embodiment, the bonding of these strands to organic materials, especially thermosetting materials, is greatly enhanced. The composites obtained from these strands and from an organic material have better mechanical properties before ageing and, over at least a certain period of time, after ageing in a corrosive medium, as compared to composites obtained from the same organic material and from common alkali-resistant glass strands not coated with the size according to the present invention, (such as alkali-resistant glass strands coated with sizes which include, as silane, a silane other than that according to the present invention). The alkali-resistant glass strands coated with the size according to the present invention are thus advantageous not only for the direct reinforcement of corrosive inorganic materials, including alkaline materials such as cement, but also, and even more surprisingly and advantageously, for the reinforcement of organic materials which may or may not be intended to be subjected to high stresses in a corrosive medium (for example in cement).

It should also be pointed out that the alkali-resistant glass strands coated with the present composition are capable of being woven, which enables them to be used in applications such as the production of meshing for walls. This meshing has previously been produced from E glass strands covered with a protective substance (generally in the form of a concentrated emulsion of several film-forming polymers of the butadiene type, polyvinyl chloride type, acrylic type, etc.). In such applications, the use of alkali-resistant glass strands, which are already more suitable at the outset than E glass strands for the direct reinforcement of alkaline materials, such as cement, and which consequently do not require protection in this kind of application with an organic material, thus makes it possible to avoid having to use an additional protective substance.

The composites obtained from an organic material and from other glass strands coated with the size according to the present invention—such as R or E glass strands according to the present invention—also have improved mechanical properties before ageing and, for at least a certain period of time, after ageing, in at least some corrosive media, the improvement being, however, less appreciable in many cases than the improvement observed with the present alkali-resistant glass strands. In particular, the use of E glass strands according to the present invention for producing composites does not lead to an improvement with regard to the mechanical properties of the composites obtained when these composites are subjected to high stresses in acid medium. Likewise, the use of E glass strands according to the present invention in alkaline medium does not lead to a significant improvement with regard to the mechanical properties of the composites produced. Moreover, in a wet and/or NaCl salty medium, the improvement in the mechanical properties of the present composites after ageing is observed over a period of time which is much shorter in embodiments using R glass strands than in embodiments using alkali-resistant glass strands. However, the R or E glass strands embodiments make it possible to obtain composites whose mechanical properties are nevertheless particularly high because of the good adhesion at the outset between the R or E glass strands and the organic materials.

Preferably, the $R^4$ group of the silane of the present invention satisfies the following formula:

$$R^5 \phi R^6$$

in which:

$\phi$ is an unsaturated ring, preferably a phenylene ring, most preferably a para isomer, $R^6$ is an unsaturated chain conjugated with the ring, preferably, $R^6$=—$(CH=CH)_m$—H, wherein m is an integer from 1 to 4, especially for steric hindrance reasons, more preferably m=1 or 2, most preferably m=1; and $R^5$ is an aliphatic chain which includes one or more alkylene portions and optionally one or more amine group portions (wherein the one or more optional amine group portions can contribute to certain coupling interactions with the other components of the size and/or with the materials reinforced), the number of atoms in the main chain is from 4 to 20, especially for steric hindrance reasons. This chain can be linear or branched and can contain unsaturations, especially on its branches. Preferably, this aliphatic chain includes one or more alkylene and amine groups. More preferably, it comprises at least 4 carbons and remains mostly composed of alkylene groups (for example, and advantageously, this chain includes at least 3 times more alkylene groups than amine groups); most preferably, it consists of a succession of groups satisfying the following formula: —$(CH_2)_n$—NH—, wherein n is an integer which can vary depending on the groups and is preferably less than 4, and is terminated at each of its ends by an alkylene or alkyl group. For example, $R^5$=—$(CH_2)_n$—NH—$(CH_2)_{n'}$—NH—$(CH_2)_{n''}$—, where n, n' and n''≦4.

The $R^3$ group of the present silane can be a group of the $R^4$ or $R^5$ type or an alkoxy group and is preferably an alkoxy group having from 1 to 4 carbons. The alkoxy groups of the present silane are most preferably selected from ethoxy groups and methoxy groups.

According to one preferred embodiment of the present invention, the sizing composition used according to the present invention includes at least one silane as defined above, in which:

$R^1=R^2=R^3$=—$OCH_3$; 

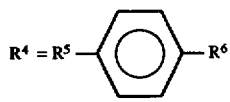

where $R^5$=—$(CH_2)_3$—NH—$(CH_2)_2$—NH—$CH_2$— and $R^6$=—CH=$CH_2$, that is to say a 1-vinylbenzyl-4-methyl-aminoethylamino propyltrimethoxysilane.

The amount of the present silane(s) contained in the sizing composition according to the present invention is generally between 0.5 and 20% by weight, preferably between 2 and 15% by weight and most preferably between 4 and 13% by weight of the dry extract of the composition. The improvement in the mechanical properties that is observed in the composites generally increases with the amount of silane (except in the case of E glass strands used in acid medium as illustrated later). Below 0.5% by weight of the present silane(s), the improvement in the mechanical properties is insignificant; below 2% by weight, the improvement is generally not very great and above 15% by weight of silane(s) according to the invention, the cost of the size becomes very high without additional improvement in the properties, and in some cases, above 20%, even showing a decrease in the mechanical properties.

In addition to the at least one silane as mentioned above, the sizing composition according to the present invention may include one or more other silanes generally acting as coupling agents, especially one or more silanes commonly used in sizes, such as gamma-methacryloxypropyltrimethoxysilane, gamma-glycidoxypropyltrimethoxysilane, etc., it being possible for these silanes to contribute to the coupling between the glass strands and the material reinforced. In that case, the amount of silane or silanes other than the silane defined according to the present invention is generally less than 12% by weight and preferably less than 5% by weight of the dry extract of the present composition. The maximum amount of silane(s), all silanes included, should not exceed 25% by weight of the dry extract of the present composition. The present sizing composition may also include other coupling agents, such as titanates or zirconates, or organic compounds promoting coupling of the glass strands to certain organic materials.

According to a preferred embodiment of the present invention, the composition coating the strands includes, in addition to the silane or silanes according to the present invention, at least one adhesive agent that normally bonds the filaments together (integrity) within the strands. This adhesive agent is preferably a compound having an epoxy functional group or groups, more preferably a polymer having at least partially polymerized functional groups and having at least one epoxy functional group. This "prepolymer" includes for example, a diepoxidized derivative of bisphenol A or F, an epoxyphenol novolak resin or epoxycresol novolak resin, a phenylglycidyl ether, a triglycidyl ether of para-aminophenol or a cyclohexanedimethanol diglycidyl ether. The combined use of at least one silane as defined according to the present invention and of at least one adhesive agent having at least one epoxy functional group makes it possible to obtain results for the composites obtained from these strands and from an organic and/or inorganic material which are further improved and surprisingly high in terms of mechanical properties both before ageing and, during at least a certain period of time, after ageing in a corrosive medium. This combination also makes it possible to obtain particularly good corrosion resistance properties (much less rapid loss of mechanical properties over time in a corrosive medium) for these composites or for the strands, especially better corrosion resistance than when a composition is used which includes, at equivalent amounts, only one of these constituents (synergistic effect).

The composition may also include one or more other adhesive agents, such as an adhesive agent having a polyester functional group or groups, such as polyvinyl acetate, in addition to or instead of the adhesive agent or agents having an epoxy functional group or groups. This latter embodiment however, is less advantageous than the embodiment using an adhesive agent having an epoxy functional group or groups, as illustrated later. The total amount of adhesive agent(s) is preferably between 0 and 85% by weight and more preferably between 50 and 75% by weight of the dry extract of the composition, with at least 85% of the amount of adhesive agents preferably being adhesive agents having an epoxy functional group (or groups).

According to one advantageous embodiment of the present invention, in which the strands are intended for the direct reinforcement of an alkaline material such as cement, the composition includes at least one silane as defined previously, optionally, at least one adhesive agent having an epoxy functional group or groups, and at least one phosphonic acid or phosphonic acid derivative. Suitable phosphonic acid or acid derivatives include potassium hexamethylenediaminetetramethyl phosphonate, potassium diethylenetriaminepentamethylene phosphonate, butanephosphonictricarboxylic acid, sodium butanephosphotricarboxylate, hydroxyethane diphosphonic acid and sodium hydroxyethanediphosphonate. In coating glass strands, the use of a composition that includes at least one silane as defined according to the present invention combined with at least one phosphonic acid or acid derivative makes it possible to obtain strands or composites having good corrosion resistance properties, especially when the glass strands are combined directly with an alkaline inorganic material, such as cement. The combined use of at least one silane as defined above, at least one phosphonic acid or acid derivative and at least one adhesive agent having an epoxy functional group or groups in the composition coating the strands makes it possible to obtain strands having a surprising resistance to ageing in at least certain corrosive media, such as an alkaline medium, especially corrosion resistance which is better than when a composition is used which includes, at equivalent amounts, only one or two of these constituents. This synergistic effect is especially noticed when the glass strands are combined directly with an alkaline inorganic material such as cement.

The amount of phosphonic acid or acid derivative is generally between 0 and 40% by weight of the dry extract of the composition and preferably, when the glass strands are intended to be combined directly with an alkaline inorganic material such as cement, between 10 and 40% by weight of the dry extract of the composition.

In addition to the components mentioned above, the present size composition can also include other components, especially components commonly used in sizing compositions, such as lubricants, or film-forming agents, textile agents, antistatic agents, emulsifiers, surface-active agents, wetting agents, etc. The proportion of these agents contained in the size composition is preferably less than 30% by weight of the dry extract of the composition. In most cases, the composition includes at least one lubricant, such as a fatty acid ester or fatty alcohol derivative, with the proportion of lubricant preferably being at least 5% by weight of the dry extract of the composition.

The composition according to the present invention can be obtained by mixing all the components at the same time or by adding the components in several steps. Generally, the silane according to the present invention is added to the composition in a hydrolysed form. After mixing the active compounds, a solvent, preferably water, may be added to the mixture to obtain the desired composition and proportions.

When the sizing composition according to the present invention is in the form of an aqueous dispersion, the dry extract of the composition is generally between 2 and 30% by weight of the composition.

The composition is generally deposited on the filaments in one step before they are assembled into strands, as explained above. However, the components of the composition coating the strands may be deposited in several steps if desired. For example, the silane according to the present invention can be deposited, in a hydrolysed form, independently of the other constituents of the composition, preferably before depositing these other constituents, so that the silane is brought directly into contact with the glass of which the strands are composed.

The loss on ignition of the strands according to the present invention is preferably from 0.2 to 4% by weight of the strands and more preferably from 0.3 to 2% by weight of the strands. These strands allow effective reinforcement of organic and/or inorganic materials and make it possible to obtain composites having improved mechanical properties in corrosive media, as explained above.

The composites obtained from the strands according to the present invention include at least one organic material and/or at least one inorganic material and glass strands, with at least some of the strands being the glass strands according to the invention. The glass strands according to the present invention are preferably combined with thermosetting materials (such as vinylesters, polyesters, phenolics, epoxides, and acrylics), more preferably with vinylesters which are more corrosion resistant than other organic materials, and/or with cementitious materials (such as cement, concrete, mortar, gypsum, and compounds formed by reaction of lime, silica and water). It is possible for the reinforcement of the cementitious materials to be effected directly or indirectly (precombining with an organic material before being added to the cement).

Having generally described this invention, a further understanding can be obtained by reference to certain specific examples which are provided herein for purposes of illustration only and are not intended to be limiting unless otherwise specified.

EXAMPLES

The following non-limiting examples illustrate the glass strands and the compositions according to the invention and make it possible to compare the mechanical properties obtained before and after ageing for composites produced from glass strands according to the invention with the mechanical properties obtained for composites produced from conventional glass strands.

COMPARATIVE EXAMPLE 1

In this example, glass filaments 14 μm in diameter were obtained by drawing streams of molten glass, this glass being an alkali-resistant glass of the following composition, expressed in weight percentages:

| | |
|---|---|
| $SiO_2$ | 61.6% |
| $Al_2O_3$ | 0.9% |
| $ZrO_2$ | 16.8% |
| CaO | 5.4% |
| $Na_2O$ | 14.7% |
| $K_2O$ | 0.3% |
| $Fe_2O_3$ | 0.05% |
| Fluorine | 0.26% |
| $TiO_2$ | 0.1% |
| $SO_3$ | 0.05% |

These filaments were coated, during their passage before being assembled into strands, with a sizing composition which included 1% by weight of a lubricant based on ethoxylated nonylphenol (marketed under the reference name "IGEPAL CO 880" by GAF), 0.15 by weight of gamma-methacryloxypropyltrimethoxysilane (marketed under the reference name "SILQUEST A 174" by OSi), the balance being water. The strands, which were obtained by assembling the filaments and which had a linear density ("Yarn count") of 300 g/km (tex), were wound in the form of cakes and then dried using hot air at 130° C. Next, these strands were extracted from the wound packages in order to produce plaques with parallel strands in accordance with the NF 57-152 standard. The resin reinforced by the strands was polyester resin M 402 marketed under this reference name by Cray-Valley, to which was added, per 100 parts by weight of polyester resin, 15 parts of a flexibilizer marketed under the reference name "F 8010 C" by Cray-Valley, 16.5 parts of styrene and 1.5 parts of an accelerator marketed under the reference name "THM 60" by Ciba-Geigy.

The mechanical properties in bending exhibited by these plaques were measured according to the Standard ISO 178 before ageing and after immersion of these plaques in water at 98° C. for 24 hours (accelerated ageing). The flexural strength, for an amount of glass extrapolated to 100%, was 1120 MPa (with a standard deviation of 122 MPa on 10 plaques) before ageing and 186 MPa (with a standard deviation of 20 MPa) after ageing.

EXAMPLE 1

The same procedure as in Comparative Example 1 was carried out, replacing the gamma-methacryloxypropyltrimethoxysilane with 1-(vinylhenzyl-4-methylaminoethylamino)propyltrimethoxysilane (added in the form of a hydrochloride in solution in methanol, this solution being marketed under the reference name "SILANE Z-6032" by Dow Corning).

The flexural strength for an amount of glass extrapolated to 100%, was 2111MPa (with a standard deviation of 159 MPa on 10 plaques) before ageing and 616 MPa (with a standard deviation of 26 MPa) after ageing.

It was observed that the use of strands according to the present invention considerably improved the flexural strength of the composites produced from the strands and from an organic material. The resistance to ageing in a wet medium was also improved, with the loss in mechanical properties after 7 days of accelerated ageing in a wet medium being much less than the loss observed using strands coated with a silane which does not satisfy the silane definition of the present invention.

EXAMPLE 2

Wound packages of alkali-resistant glass strands were produced in the same way as in Comparative Example 1, replacing the sizing composition used in this Comparative example with a sizing composition which included 0.08% by weight of 1-(vinylbenzyl-4-methylaminoethylamino) propyltrimethoxysilane (added in the form of a hydrochloride in solution in methanol), 0.25% by weight of (N-benzylaminoethyl)aminopropyltrimethoxysilane (added in the form of a hydrochloride in solution in methanol, this solution being marketed under the reference name "SILQUEST A 1128" by OSi), 1.80% by weight of diethylene glycol adipate adhesive agent marketed under the reference name "NAXOL 2500 SH" by Scott Bader, 0.42% by weight of a polyethylene glycol lubricant and emulsifier marketed under the reference name "BREOX 2000" by BP Chemicals, the balance essentially being water. The dry extract was approximately 2.6% by weight of the composition.

Next, the strands were extracted from the wound packages in order to produce plaques having parallel strands in accordance with the Standard NF 57-152. The resin reinforced with the strands was the vinylester resin Derakane 41145 marketed under this reference name by Dow Chemicals, to which was added, per 100 parts by weight of vinylester resin, 0.75 parts by weight of a catalyst marketed under the reference name "TRIGONOX 239" by Akzo and 0.08% by weight of an accelerator marketed under the reference name "NL 51P" by Akzo.

The mechanical properties in bending exhibited by these plaques were measured according to the Standard ISO 178 after having subjected the specimens to an imposed deformation in bending in a liquid corrosive medium at 40° C. for periods of from 3 to 7 days. The flexural strengths (expressed in MPa), for an amount of glass extrapolated to 100%, measured after these "stress corrosion" tests respectively in a solution of 1N sulphuric acid, in a solution of 1N sodium hydroxide, in distilled water and in a salt solution containing 37 g of NaCl salt per liter, are given in Table I below, the standard deviations on 6 test pieces being indicated in brackets.

EXAMPLE 3

The same procedure was carried out as in Example 2, this time modifying, in the sizing composition used, the amount of 1-vinylbenzyl-4-methylaminoethyl-amino propyltrimethoxysilane (in this case, it represented 0.2% by weight of the composition) and the amount of (N-benzylaminoethyl) aminopropyltrimethoxy-silane (in this case, it represented 0.1% by weight of the composition). The results are given in Table I.

An improvement in the flexural strength of the composites was observed after 3 and 7 days of accelerated ageing in corrosive medium, whatever the medium, when the amount of silane according to the invention in the composition coating the strands used was increased.

EXAMPLE 4

The same procedure was carried out as in Example 2, this time using glass strands obtained from an E glass of the following composition, expressed in weight percentages:

| | |
|---|---|
| SiO$_2$ | 55% |
| Al$_2$O$_3$ | 15% |
| B$_2$O$_3$ | 7% |
| MgO | 3% |
| CaO | 19% |
| Na$_2$O | 0.3% |
| K$_2$O | 0.2% |
| Fe$_2$O$_3$ | 0.3% |
| Fluorine | 0.3% |

The results are given in Table I.

EXAMPLE 5

The same procedure was carried out as in Example 3, this time using glass strands obtained from the E glass whose composition is given in Example 4. The results are given in Table I.

An improvement in the flexural strength of the composites was observed after 3 to 7 days of accelerated ageing in distilled water or in a salt solution when the amount of silane according to the invention in the composition coating the strands used was increased.

EXAMPLE 6

The same procedure was carried out as in Example 2, this time using glass strands obtained from an R glass of the following composition, expressed in weight percentages:

| | |
|---|---|
| SiO$_2$ | 60% |
| Al$_2$O$_3$ | 25% |
| MgO | 6% |
| CaO | 9% |

The results are given in Table I.

EXAMPLE 7

The same procedure was carried out as in Example 3, this time using glass strands obtained from the R glass whose composition is given in Example 6.

The results are given in Table I.

An improvement in the flexural strength of the composites was observed after 3 days of accelerated ageing in corrosive medium, whatever the medium, and after 7 days of accelerated ageing in acid medium or in alkaline medium. The use of the strands according to the invention thus makes it possible to slow down the degradation of the strands and composites in corrosive media.

EXAMPLE 8

The same procedure was carried out as in Example 2, replacing the sizing composition used in this example with a sizing composition which included 0.5% by weight of 1-(vinylbenzyl-4-methylaminoethylamino) propyltrimethoxysilane (added in the form of a hydrochloride); 0.1% by weight of polyazamidesilane marketed under the reference name "SILQUEST A 1387" by OSi; 3.3% by weight of the polyester adhesive agent marketed under the reference name NAXOL 2500 SH" by Scott Bader; and 0.6% by weight of a polyethylene glycol lubricant marketed under the reference name "BREOX 2000" by BP Chemicals, the balance essentially being water. The dry extract was 4.5% by weight.

The mechanical bending properties of the plaques produced in the same way as in Example 2 were measured according to Standard ISO 178 before ageing and after having subjected the specimens to an imposed deformation in bending in a liquid corrosive medium at 40° C. for 7 days. The flexural strengths (expressed in MPa), for an amount of glass extrapolated to 100%, measured after these stress corrosion tests respectively in a solution of 1N sulphuric acid and in a solution of 1N sodium hydroxide, are given in the Table II below.

EXAMPLE 9

The same procedure as in Example 8 was carried out, replacing, in the sizing composition used, the polyester adhesive agent with an epoxy adhesive agent marketed under the reference name "EPI-REZ 3510 W 60" by Shell.

The results are given in Table II.

It may be observed that the combined use of a silane according to the invention and an adhesive agent having epoxy functional groups in the composition coating the strands according to the invention makes it possible to obtain surprisingly high results in terms of mechanical properties before and after 7 days of ageing in corrosive medium, for the composites obtained from these strands and from an organic material and makes it possible to obtain strands and composites which exhibit extraordinarily good corrosion resistance.

COMPARATIVE EXAMPLE 2

Wound packages of alkali-resistant glass strands were produced in the same way as in Comparative Example 1, replacing the sizing composition used in this example with a sizing composition which includes 0.25% by weight of (N-bensylaminoethyl)aminopropyltrimethoxysilane (added in the form of a hydrochloride in solution, this solution being marketed under the reference name "DYNASILAN 1161" by Hdls) 10% by weight of an adhesive agent based on a high-molecular weight polyvinyl acetate (added in the form of a solution marketed under the reference name "VINA-MUL R 84146" by VINAMUL), 2% by weight of a lubricant based on an ethoxylated sorbitan monooleate marketed under the reference name "TWEEN 80" by ICI and on fatty acid marketed under the reference name "LUTOSTAT N 68" by Sidobre Sinnova, the balance essentially being water. The dry extract was approximately 12% by weight.

Next, the strands were extracted from the wound packages and then held captive in a paste of artificial Portland cement of the CPA-CEM I 42.5 type (Standard NF P15-301) having a water/cement ratio of 0.4 and taking care that some of the strand extended beyond the wet cement.

Next, the cement was hardened at room temperature for 1 hour and then in water for 23 hours. The tensile strength of the strands held in cement blocks was measured on an Instron tensile tester before and after ageing in water at 80° C. for 4 days. The results (expressed in MPa) are given in Table III. The residual strength (that is to say the strength after ageing, expressed as a percentage of the initial strength) is also indicated.

EXAMPLE 10

The same procedure as in comparative Example 2 was carried out using an identical sizing composition but stripped of the (N-benzylaminoethyl) aminopropyltrimethoxysilane and furthermore including 1-(vinylbenzyl-4-methylaminoethylamino) propyltrimethoxysilane at amounts of 5% by weight with respect to the dry extract of the composition and including a smaller amount of lubricant and of adhesive agent so as to have the same dry extract of 12% by weight.

The results are given in Table III.

EXAMPLE 11

The same procedure as in Example 10 was carried out using a sizing composition which was identical but which included, instead of the polyvinyl acetate adhesive agent, at the same amount, an adhesive agent based on diglycidyl ether of bisphenol A (marketed under the reference name "NEOXIL 8294" by DSM Italia), this composition having a dry extract of 12% by weight.

The results are given in Table III.

EXAMPLE 12

The same procedure as in Example 11 was carried out using a sizing composition which was identical but which furthermore included a hydroxyethanediphosphonic acid marketed under the reference name "MAQUOL P 210" by Protex, at an amount of 18% by weight with respect to the dry extract of the composition and which included a smaller amount of lubricant and of adhesive agent so as to have the same dry extract of 12% by weight.

The results are given in Table III.

An improvement in the tensile strength of the strands before and after 4 days of accelerated ageing was observed when these strands were coated with a composition according to the present invention. This improvement was greater when the composition also included an adhesive agent having an epoxy functional group or groups and/or a phosphonic acid. It was also observed that the corrosion resistance in alkaline medium was much greater (smaller loss in mechanical properties in ageing) when the composition included, in addition to at least one silane according to the present invention, at least one adhesive agent having an epoxy functional group or groups and at least one phosphonic acid.

The strands according to the invention may be used for the production of various composites and especially for the direct reinforcement of cement (applications: meshing for walls, etc.) or for the indirect reinforcement of cement (applications: substitution of rebars for concrete with pultruded rods, etc.).

TABLE I

|  |  | Example 2 | Example 3 | Example 4 | Example 5 | Example 6 | Example 7 |
|---|---|---|---|---|---|---|---|
| Acid medium | 3 days | 810 (40) | 1602 (172) | 1304 (431) | 518 (243) | 1522 (402) | 2001 (199) |
|  | 7 days | 681 (31) | 834 (65) | 0 | 0 | 1207 (255) | 1508 (233) |
| Sodium hydroxide medium | 3 days | 864 (85) | 1340 (108) | 2129 (38) | 2142 (217) | 1524 (372) | 1642 (393) |
|  | 7 days | 627 (94) | 657 (152) | 1979 (118) | 1822 (229) | 1325 (320) | 1535 (251) |
| Dis- | 3 | 795 | 1536 | 2067 | 2241 | 1530 | 1986 |

TABLE I-continued

|  |  | Example 2 | Example 3 | Example 4 | Example 5 | Example 6 | Example 7 |
|---|---|---|---|---|---|---|---|
| tilled water | days | (47) | (82) | (220) | (102) | (300) | (139) |
|  | 7 days | 634 | 771 | 1835 | 2144 | 1142 | 1109 |
| medium | days | (37) | (67) | (83) | (151) | (254) | (165) |
| NaCl salt | 3 days | 935 (101) | 1670 (246) | 2065 (133) | 2231 (123) | 1512 (352) | 1935 (315) |
| medium | 7 days | 679 (51) | 931 (72) | 2019 (150) | 2235 (119) | 1273 (257) | 1275 (291) |

TABLE II

|  |  | Example 8 | Example 9 |
|---|---|---|---|
| Acid medium | Before ageing | 2195 | 2275 |
|  | 7 days | 835 | 2230 |
| Sodium hydroxide medium | Before ageing | 2195 | 2275 |
|  | 7 days | 655 | 2125 |

TABLE III

|  | Comparative Example 2 | Example 10 | Example 11 | Example 12 |
|---|---|---|---|---|
| Strength before ageing (MPa) | 1032 | 1422 | 1830 | 1621 |
| Strength after 4 days (MPa) | 303 | 385 | 640 | 736 |
| Residual strength (%) | 29 | 27 | 35 | 45 |

This application is based on French Patent Application 95/10316, filed with the French Patent Office on Sep. 1, 1995, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Reinforcement glass strands comprising glass strands coated with a sizing composition comprising at least one silane satisfying the following formula:

$$Si(R^1)(R^2)(R^3)(R^4)$$

wherein:

$R^1$ and $R^2$ are each, independently, an alkoxy group;

$R^3$ is an alkoxy group or a hydrocarbon radical that optionally contains only one or more nitrogens;

$R^4$ is a hydrocarbon radical that optionally contains only one or more nitrogens, and includes at least one unsaturated ring substituted with at least one unsaturated chain conjugated with the unsaturated ring.

2. Reinforcement glass strands according to claim 1, wherein $R^4$ satisfies the following formula:

$$R^5 \phi R^6$$

in which:

$\phi$ is a phenylene ring;

$R^6$ is a group of formula $-(CH=CH)_m-H$, wherein m is an integer from 1 to 4;

$R^5$ is a linear or branched aliphatic chain of one or more alkylene groups and optionally one or more amine groups, wherein the aliphatic chain has from 4 to 20 atoms in its main chain, and wherein $R^3$ is the same as $R^4$ or $R^5$ or an alkoxy group.

3. Reinforcement glass strands according to claim 1, wherein said sizing composition further comprises at least one adhesive agent having at least one epoxy functional group.

4. Reinforcement glass strands according to claim 1, wherein said sizing composition further comprises at least one phosphonic acid or phosphonic acid derivative.

5. Reinforcement glass strands according to claim 1, wherein said sizing composition further comprises at least one adhesive agent having at least one epoxy functional group and at least one phosphonic acid or phosphonic acid derivative.

6. Reinforcement glass strands according to claim 1, wherein said glass strands are prepared from a glass selected from the group consisting of alkali-resistant glasses, E glasses, R glasses, S glasses and acid-resistant glasses.

7. Reinforcement glass strands according to claim 6, wherein said glass is alkali-resistant glass.

8. Reinforcement glass strands according to claim 1, wherein said glass strands are prepared from a glass having a composition comprising:

62–75% $SiO_2$;
7–11% $ZrO_2$;
13–21% $R_2O$;
1–10% $R'O$;
0–4% $Al_2O_3$;
0–6% $B_2O_3$;
0–5% $Fe_2O_3$;
0–2% $CaF_2$; and
0–4% $TiO_2$;

wherein $R_2O$ represents one or more alkali-metal oxides, and R'O is one or more components chosen from the alkaline-earth metal oxides, ZnO and MnO, all percentages being in mol %.

9. Reinforcement glass strands according to claim 8, wherein $R_2O$ is $Na_2O$, containing from 0 to 2 mol % $Li_2O$.

10. A sizing composition for glass strands, comprising at least one silane satisfying the following formula:

$$Si(R^1)(R^2)(R^3)(R^4)$$

wherein:

$R^1$ and $R^2$ are each, independently, an alkoxy group;
$R^3$ is an alkoxy group or a hydrocarbon radical that optionally only contains one or more nitrogens;
$R^4$ is a hydrocarbon radical that optionally contains only one or more nitrogens, and includes at least one unsaturated ring substituted with at least one unsaturated chain conjugated with the unsaturated ring.

11. The sizing composition according to claim 10, wherein $R^4$ satisfies the following formula:

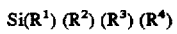

in which:

φ is a phenylene ring;
$R^6$ is a group of formula $-(CH=CH)_m-H$, wherein m is an integer from 1 to 4;
$R^5$ is a linear or branched aliphatic chain including one or more alkylene groups and optionally one or more amine groups, wherein the aliphatic chain has from 4 to 20 atoms in a main chain, and wherein $R^3$ is the same as $R^4$ or $R^5$ or an alkoxy group.

12. The sizing composition according to claim 10, wherein said sizing composition further comprises at least one adhesive agent having at least one epoxy functional group.

13. The sizing composition according to claim 10, wherein said sizing composition further comprises at least one phosphonic acid or phosphonic acid derivative.

14. The sizing composition according to claim 10, wherein said sizing composition further comprises at least one adhesive agent having at least one epoxy functional group and at least one phosphonic acid or phosphonic acid derivative.

15. A composite material comprising at least one organic material, one inorganic material or both in admixture with glass strands, wherein said glass strands are coated with a sizing composition comprising at least one silane satisfying the following formula:

$$Si(R^1)(R^2)(R^3)(R^4)$$

wherein:

$R^1$ and $R^2$ are each, independently, an alkoxy group;
$R^3$ is an alkoxy group or a hydrocarbon radical that optionally contains only one or more nitrogens;
$R^4$ is a hydrocarbon radical that optionally contains only one or more nitrogens, and includes at least one unsaturated ring substituted with at least one unsaturated chain conjugated with the unsaturated ring.

16. The composite material according to claim 15, wherein $R^4$ satisfies the following formula:

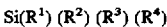

in which:

φ is a phenylene ring;
$R^6$ is a group of formula $-(CH=CH)_m-H$, wherein m is an integer from 1 to 4;
$R^5$ is a linear or branched aliphatic chain including one or more alkylene groups and optionally one or more amine groups, wherein the aliphatic chain has from 4 to 20 atoms in a main chain, and wherein $R^3$ is the same as $R^4$ or $R^5$ or an alkoxy group.

17. The composite material according to claim 15, wherein said sizing composition further comprises at least one adhesive agent having at least one epoxy functional group.

18. The composite material according to claim 15, wherein said sizing composition further comprises at least one phosphonic acid or phosphonic acid derivative.

19. The composite material according to claim 15, wherein said sizing composition further comprises at least one adhesive agent having at least one epoxy functional group and at least one phosphonic acid or phosphonic acid derivative.

20. The composite material according to claim 15, wherein said at least one organic material, inorganic material or both comprises at least one cementitious material.

21. Reinforcement glass strands comprising glass strands coated with a sizing composition comprising at least one silane satisfying the formula:

$$Si(R^1)(R^2)(R^3)(R^4)$$

wherein $R^1$ and $R^2$ are each, independently, an alkoxy group;
$R^3$ consists of (i) an alkoxy group or (ii) a hydrocarbon radical optionally containing at least one nitrogen atom; and
$R^4$ consists of a hydrocarbon radical optionally containing at least one nitrogen atom and containing at least one unsaturated ring substituted with at least one unsaturated chain conjugated with the unsaturated ring.

* * * * *

UNITED STATES PATENT AND TRADEMARK OFFICE
CERTIFICATE OF CORRECTION

PATENT NO. : 5,736,246
DATED : April 7, 1998
INVENTOR(S) : Eric AUGIER et al

It is certified that error appears in the above-identified patent and that said Letters Patent is hereby corrected as shown below:

On the title page, in [57] ABSTRACT, second to the last line, "mproved" should read --improved--.

Column 15, line 24, "62-75% SIO$_2$," should read --62-75% SiO$_2$--

Column 15, line 54, "R$^{5\phi R6}$" should read --R$^5$ $\phi$ R$^6$--.

Signed and Sealed this

Fourth Day of May, 1999

*Attest:*

Q. TODD DICKINSON

*Attesting Officer*     *Acting Commissioner of Patents and Trademarks*